(12) United States Patent
Clavadetscher et al.

(10) Patent No.: US 8,679,070 B2
(45) Date of Patent: Mar. 25, 2014

(54) MODULAR ADMINISTRATION SYSTEM

(75) Inventors: Jürg Clavadetscher, Ortschwaben (CH); Edgar Hommann, Grossaffoltern (CH)

(73) Assignee: TecPharma Licensing AG, Burgdorf (CH)

( * ) Notice: Subject to any disclaimer, the term of this patent is extended or adjusted under 35 U.S.C. 154(b) by 285 days.

(21) Appl. No.: 12/541,243

(22) Filed: Aug. 14, 2009

(65) Prior Publication Data

US 2010/0152661 A1   Jun. 17, 2010

Related U.S. Application Data

(63) Continuation of application No. PCT/CH2007/000113, filed on Mar. 2, 2007.

(51) Int. Cl.
*A61M 5/315* (2006.01)
(52) U.S. Cl.
USPC ........... 604/218; 604/131; 604/145; 604/155; 604/228; 604/232; 604/235
(58) Field of Classification Search
USPC ......... 604/131, 145, 155, 218, 223, 228, 232, 604/235
See application file for complete search history.

(56) References Cited

U.S. PATENT DOCUMENTS

| | | | | |
|---|---|---|---|---|
| 3,964,482 A | * | 6/1976 | Gerstel et al. | 604/890.1 |
| 4,560,979 A | * | 12/1985 | Rosskopf | 340/540 |
| 5,279,544 A | * | 1/1994 | Gross et al. | 604/20 |
| 6,256,533 B1 | * | 7/2001 | Yuzhakov et al. | 604/21 |
| 6,565,532 B1 | * | 5/2003 | Yuzhakov et al. | 604/142 |
| 6,603,998 B1 | * | 8/2003 | King et al. | 604/20 |
| 6,743,211 B1 | * | 6/2004 | Prausnitz et al. | 604/239 |
| 6,770,480 B1 | * | 8/2004 | Canham | 435/458 |
| 7,537,579 B2 | * | 5/2009 | Price | 604/65 |
| 2002/0099356 A1 | * | 7/2002 | Unger et al. | 604/501 |
| 2003/0009133 A1 | | 1/2003 | Ramey | |
| 2004/0044308 A1 | * | 3/2004 | Naimark et al. | 604/103 |
| 2005/0197626 A1 | * | 9/2005 | Moberg et al. | 604/131 |
| 2006/0004327 A1 | * | 1/2006 | Fournie et al. | 604/65 |
| 2006/0015066 A1 | * | 1/2006 | Turieo et al. | 604/136 |
| 2007/0010789 A1 | | 1/2007 | Peter et al. | |

FOREIGN PATENT DOCUMENTS

| | | |
|---|---|---|
| EP | 1 704 886 | 9/2006 |
| WO | 00/25844 | 5/2000 |
| WO | 2006/114012 | 11/2006 |

* cited by examiner

*Primary Examiner* — Jason Flick
*Assistant Examiner* — Scott Medway
(74) *Attorney, Agent, or Firm* — Dorsey & Whitney LLP; David E. Bruhn, Esq.

(57) ABSTRACT

A modular administration appliance including a reusable base unit and a replaceable cartridge detachably connected to the base unit and including a container for a substance and a rotatable transmission element, the base unit including a drive device by which a rotary movement is transmitted between the base unit and the cartridge, and a driving element displaceable in a rotary movement about a rotational axis by the drive device, wherein a rotation of the transmission element causes the ejection of at least a portion of the substance from the container. In some embodiments, the transmission element at least partially surrounds the drive device, and/or the drive element and the transmission element are detachably connectable to each other for transmitting the rotational movement.

16 Claims, 6 Drawing Sheets

MODULAR ADMINISTRATION SYSTEM

CROSS-REFERENCED RELATED APPLICATIONS

This application is a continuation of International Patent Application No. PCT/CH2007/000113 filed Mar. 2, 2007, the entire contents of which are incorporated herein by reference.

BACKGROUND

The present invention relates to devices for injecting, infusing, administering, delivering or dispensing a substance, and to methods of making and using such devices. More particularly, it relates to an appliance for administering a fluid product, e.g. a medication in liquid form. This type of appliance may be referred to herein by the designation "administration appliance," and it also may be thought of and/or referred to by using terms such as medical device, injection device, administration device, injection pen, infusion device, and the like.

Various diseases may make it necessary to administer a liquid medication to a patient over a prolonged period of time, e.g., an insulin preparation or a blood-thinning medication such as heparin. Compact, portable administration appliances are known for this purpose, which patients always carry with them, close to their bodies. The medication container in such administration appliances is most often a carpule, i.e., a glass container incorporating a sliding plug or piston. The carpule (also referred to often as an ampoule or ampule or vial) is connected with an infusion set, the syringe of which empties into the bodily tissue of the patient. A suitable drive or power source, e.g., a spring drive or an electric motor, advances the plug into the carpule, thereby ejecting the medication from the carpule. After a carpule has been emptied, it is removed from the administration appliance and replaced by a new carpule.

In many portable administration appliances, the plug is advanced in the carpule by a threaded rod, which acts as a piston rod on the plug. A rotatable nut secured against displacement runs on the threaded rod, and is driven by an electric motor. By a rotation of the nut, the threaded rod is advanced. Generally, the electric motor is situated next to the carpule to limit the length of the administration appliance, and simplify replacement of the carpule.

U.S. Pat. No. 6,248,093 discloses an administration appliance in which the drive motor and the transmission are arranged coaxially with the medication reservoir. The plug of the medication reservoir is advanced by a sleeve-like feed element, which is connected by an inner thread with a drive screw driven by the motor, and thereby linearly advanced. In its initial position, the feed element at least partially envelops the motor transmission. The feed element is part of the base unit, while the plug is part of the replaceable medication reservoir. Therefore, the feed element and plug can be detached from each other. To prevent unintentional ejection of the medication due to ambient pressure fluctuations, the feed element and the plug are connected in such a way that the connection can also absorb tensile forces during operation of the administration appliance. In this way, the plug is forced to follow the motion of the feed element, and pressure fluctuations cannot advance the plug further than prescribed by the position of the feed element. During replacement of the medication reservoir, the plug and the feed element are detached from each other in a rotational motion. The feed element is then returned to its initial position by the motor. On the one hand, this arrangement requires a relatively complicated connection between the plug and the feed element. On the other hand, it is necessary to return the feed element after the end of the administration. In addition, special measures must be taken for cases in which an incompletely filled medication reservoir is used.

Handling the carpules or medication containers or vials requires some dexterity, since they usually consist of glass, and are hence easily damaged. In addition, sterility is not always guaranteed while replacing the carpule. Therefore, administration appliances are also known in which the medication is present in a disposable cartridge, which is easier to insert into a base unit than is possible with a carpule, and contains other elements in addition to the medication container, which might come into contact with the medication, e.g., a luer lock connector for the infusion set. As a result, such a cartridge is more reliable and hygienic to use. As soon as the medication in the cartridge has been used, the latter is completely removed from the base unit, and a new cartridge is inserted into the base unit.

SUMMARY

An object of the present invention is to provide a modular administration appliance consisting of modules or components including a base unit and a relaceable cartridge that is able to be connected to the base unit, which enables a simple connection between the base unit and the cartridge, and which avoids having to reset or reposition an element or elements of the base unit when replacing a cartridge.

In one embodiment, the present invention comprises a modular administration appliance or device comprising a reusable base unit and a replaceable cartridge detachably connected to the base unit and comprising a container for a substance and a rotatable transmission element, the base unit comprising a drive device by which a rotary movement is transmitted between the base unit and the cartridge, and a driving element displaceable in a rotary movement about a rotational axis by the drive device, wherein a rotation of the transmission element causes at least a portion of the substance to move from the container. In some embodiments, the transmission element at least partially surrounds the drive device, and/or the drive element and the transmission element are detachably connectable to each other for transmitting the rotational movement.

In one embodiment, the present invention comprises a modular administration appliance provided with a reusable base unit comprising a drive device and a replaceable cartridge that is detachably connected to the base unit and comprises a product container. A rotary movement is transmitted between the base unit and the cartridge. To this end, the base unit comprises a driving element which can be displaced in a rotary movement about a rotational axis by means of the drive device, and the cartridge comprises a rotatable transmission element which is embodied in such a way that a rotation of the transmission element causes the ejection of the medicament to be administered. In one preferred form or embodiment, the transmission element at least partially surrounds the drive device.

In one embodiment, the present invention comprises an appliance for administering a fluid product, comprising a reusable base unit with a drive device, a replaceable cartridge detachably connectable with the base unit and comprising a container for the fluid product, wherein the base unit has a drive element that is able to be displaced by the drive device into a rotational movement around a rotational axis, the cartridge further comprises a rotatable transmission element complementary to the drive element, such that a rotation of the transmission element causes fluid product to move from the product container, and the drive element and the transmission element are detachably connectable to each other for transmitting the rotational movement.

In some embodiments, an appliance or device in accordance with the present invention comprises a reusable base unit with a drive device as well as a replaceable cartridge detachably connectable with the base unit, with a product container for the fluid product, i.e., the appliance comprises a number of separate or separable and connectable and detachable components, modules or units e.g. a modular structure. A rotational movement is able to be transmitted between the base unit and the cartridge. To this end, the base unit has a driving element, which is able to be displaced into a rotational movement around a rotational axis by the drive device. The cartridge comprises a rotatable transmission element complementary to and/or cooperative with the driving element, which is designed such that a rotation of the transmission element causes an ejection or movement of the fluid product from the product container. The drive element and the transmission element are able to be detachably connected with each other for transmitting the rotational movement.

While feed movements (which also may be thought of and/or referred to as a driving movement, a dispensing movement, an injection movement, etc.) are generally known in the art, in the present invention a rotational movement is transmitted between the base unit and the cartridge. This makes it easy to establish the connection between the cartridge and the base unit, since a coupling of two rotatable elements for transmitting a rotational movement is easier to realize than a compression and tensile stress-resistant connection between a piston rod and a plug. In addition, cartridge replacement is simplified. If the cartridge is to be replaced, it can easily be removed from the base unit, and a new cartridge can be inserted without having to reposition or return the drive device beforehand.

In some preferred embodiments of the present invention, to simplify the connection between the cartridge and the base unit, the drive element and the transmission element are designed so that they can shift relative to each other along the rotational axis. In this way, the drive element and the transmission element can be telescoped for easy connection. In addition, this allows the transmission element to move axially during operation. By contrast, the drive element and the transmission element are interlocked in a plane perpendicular to the rotational axis. In other words, areas of the drive element and the transmission element mutually envelop each other in such a plane. As a result, areas of the drive element alternate with areas of the transmission element along a suitable circle in the circumferential direction.

In some embodiments, the transmission element can be guided by a thread such that a rotational movement of the transmission element leads to a screw movement of the transmission element in the cartridge. In this way, the rotational movement of the drive element (in some embodiments, a purely rotational movement) results in a movement of the transmission element with a translational component in the axial direction, e.g., which can be used directly or indirectly to advance a plug or piston associated with the product container. However, the transmission element could instead also perform a pure rotational movement, which results in the ejection of the product from the product container in another way.

In one embodiment, the transmission element is configured as a sleeve, which at least partially envelops the drive element when assembled, and engages the drive element on its inside. In other words, the transmission element extends generally around the circumference of the drive element (viewed in a plane perpendicular to the rotational axis). In some embodiments, the inside of the sleeve is provided with one or more longitudinal grooves or longitudinal ribs, which run or extend parallel to the rotational axis, and the outside of the drive element exhibits a structure complementary thereto, i.e., a structure suitable for engaging the longitudinal grooves or longitudinal ribs. For example, in some embodiments, the structure can involve one or more radially outwardly projecting catches or longitudinal ribs. This construction makes it easy to perform a relative movement between the transmission element and the drive element in the axial direction.

In some embodiments, the transmission element will be movable between an initial position assumed by the transmission element before evacuation or movement of the product container begins, and a final position assumed by the transmission element after the product container has been emptied. Space may be saved by having the transmission element envelop at least part of the drive device in the initial position. In other words, in some preferred embodiments, the transmission element extends around the circumference of part of the drive device (viewed in a plane perpendicular to the rotational axis).

In some preferred embodiments, the drive device encompasses an electric motor and a transmission connected thereto, which transmits the drive movement of the motor into a rotational movement of the drive element. In one space-saving arrangement, the motor and the transmission are arranged one in back of the other along the rotational axis, and the transmission element envelops at least a part of the transmission, at least in the initial position.

In some embodiments, the drive device can be accommodated at least in part in a finger-like area of the base unit extending along the rotational axis, wherein the cartridge, when assembled, at least partially envelops the finger-like area of the base unit. This results in a simple connection between cartridge and base unit on the one hand, and yields a space-saving arrangement on the other hand.

To achieve a stable connection between the cartridge and the base unit, in some preferred embodiments the base unit exhibits a holding area that runs or extends laterally displaced relative to the finger-like area in such a way that the cartridge, when secured to the base unit, exhibits an area arranged between the finger-like area and the holding area in a lateral direction. In this way, the cartridge and the base unit mutually envelop each other, and a stable connection is achieved between these units or modules. In addition, the holding area can incorporate additional components, such as a power source, e.g. in the form of a battery, and control electronics.

In some preferred embodiments, the cartridge comprises a fluid reservoir with a movable plug. The transmission element is then connected with the plug such that rotating the transmission element advances the plug. This can involve a pure translational movement of the plug, or a combined translation and rotation, e.g. a screw movement or motion. In the latter case, the plug and the transmission element can be fabricated together as a single piece.

In some embodiments, the fluid reservoir can be the product container itself. In some preferred embodiments, a hydraulic system is used to transmit the advance of the plug indirectly to the product container, and the fluid reservoir then serves as a hydraulic reservoir for the hydraulic fluid. In this case, the cartridge encompasses a hydraulic connection between the hydraulic reservoir and a displacement reservoir that acts in conjunction with the product container, wherein the hydraulic reservoir, the hydraulic connection and the displacement reservoir are arranged such that the feed (or dispensing, ejecting, infusing or injection) movement of the plug moves the hydraulic fluid from the hydraulic reservoir through the hydraulic connection and into the displacement reservoir, thereby causing the ejection of the fluid product from the product container.

DETAILED DESCRIPTION

With regard to fastening, mounting, attaching or connecting components of the present invention, unless specifically described as otherwise, conventional mechanical fasteners and methods may be used. Appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1:
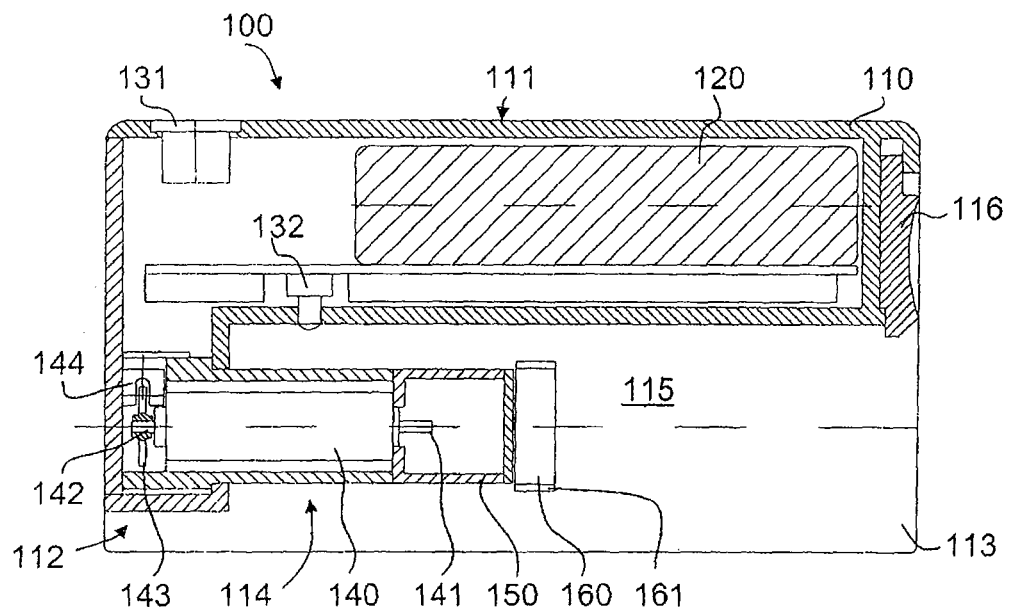
FIG. 1 is a longitudinal sectional view of one embodiment of a base unit of an embodiment of an administration appliance in accordance with the present invention.
Figures 2, 3:
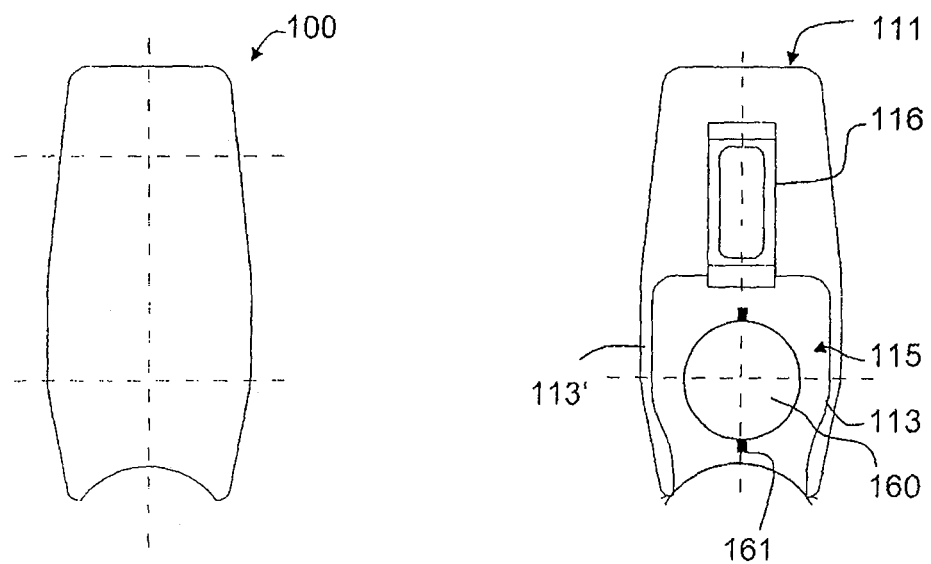
FIG. 2 is a side view of the base unit of FIG. 1, as viewed to the right in FIG. 1.
FIG. 3 is a side view of the base unit of FIG. 1, as viewed to the left.

The drawings show an embodiment of an administration appliance according to the present invention. The administration appliance encompasses a reusable base unit or module 100, which is depicted by itself in FIGS. 1 to 3, as well as a replaceable cartridge unit or module 200 complementary thereto, which is depicted by itself in FIGS. 4 and 5. FIGS. 6 to 13 show the administration appliance as assembled from the these.

Directional designations (which are, unless otherwise noted, intended to be descriptive not limiting) will be used as follows to denote directions within the administration appliance of the present invention. The distal direction should be understood as the direction in which the movable elements of the administration appliance move during administration of the medication. As will be described in even greater detail below, this movement is deflected by 180 degrees inside the administration appliance. Therefore, the distal direction corresponds to varying absolute spatial directions for different parts of the administration appliance. The proximal direction is correspondingly defined as the direction opposite the distal direction. A lateral direction is a direction perpendicular thereto.

The base unit includes a casing 110. The latter exhibits a relatively, long stretched out, essentially rounded square or prismatic holding area 111. A support area 112 for the cartridge extends in a lateral direction from one end of the holding area, projecting essentially perpendicularly from it. As a result, the casing initially exhibits an generally L-shaped configuration in the longitudinal section in FIG. 1. An generally circularly cylindrical, finger-like structure 114 (described in greater detail below) extends from out of the support area 112 in a distal direction parallel to the holding area 111. This structure is flanked laterally on either side by two wing areas 113, 113', which are readily discernible in FIG. 3. Hence, the holding area 111, the support area 112, and the wing areas 113, 113' border a receiving area 115 for the cartridge, into which the finger-like structure 114 extends.

The finger-like structure 114 contains a drive motor 140, the shaft 141 of which is routed out of the motor casing at both ends. The distal end of the shaft is connected with a transmission 150, which is arranged coaxially with the motor, also in the finger-like structure 114. The transmission reduces the rotation of the motor shaft 141, thereby transmitting the rotational movement reduced in this way to a drive element 160, which is arranged at the distal end of the finger-like area 114. The drive element 160 consists of a wheel, whose circumferential surface accommodates two diametrically opposed drive element fingers 161.

The casing 110 also incorporates an electric battery 120, as well as suitable control electronics (not shown in the drawings). The control electronics are used to actuate the motor 140 in such a way that its shaft performs a preset number of revolutions per unit of time. To determine the actual rotational angle, the control electronics receive signals from an encoder 144, which works in conjunction with an encoder wheel 143 secured to the proximal end of the motor shaft 141. As the encoder wheel turns, the encoder generates electrical signals, which make it possible to determine the traversed rotational angle or the number of revolutions of the motor shaft. For example, this can be done optically. Such encoders are known and commercially available.

Figure 4:
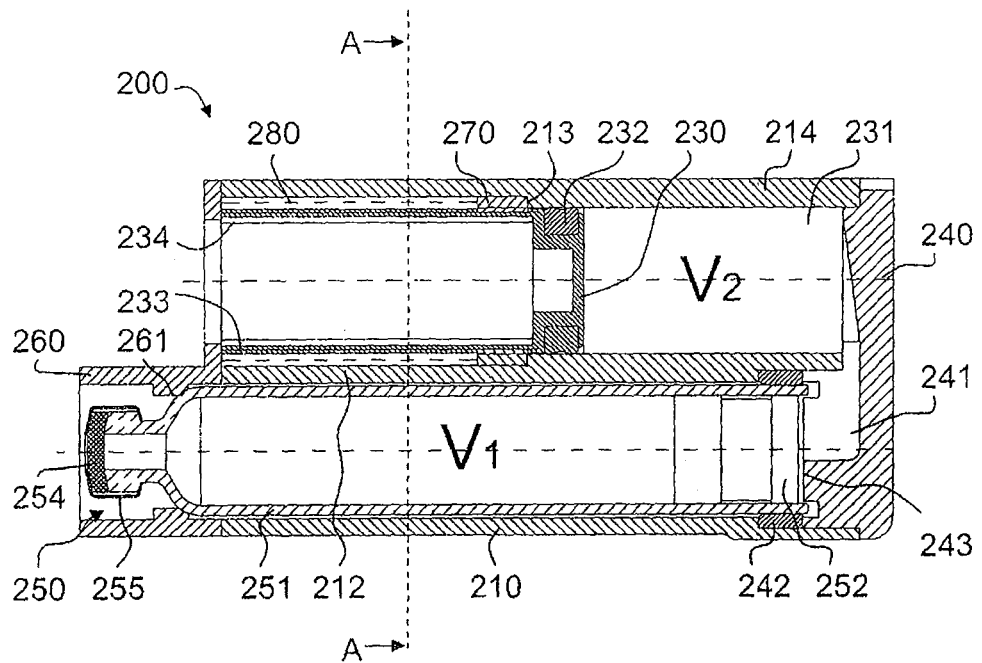
FIG. 4 is a longitudinal sectional view of an embodiment of a replaceable cartridge in accordance with the present invention.
Figure 5:
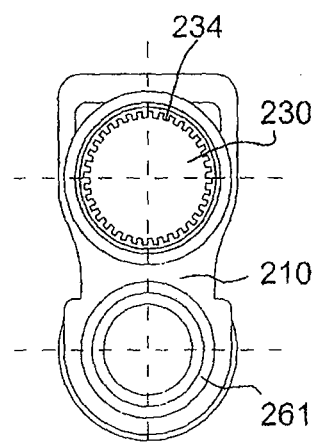
FIG. 5 is a side view of the cartridge, as viewed to the right in FIG. 4.

The base unit 100 can be connected with the replaceable cartridge 200, which is depicted in FIGS. 4 and 5. The cartridge 200 comprises a cartridge casing 210, the outer shape of which is complementary to the casing 110 of the base unit 100. This makes it possible to insert the cartridge into the receiving area 115 of the base unit 100, as described below.

A separating wall 212 divides the cartridge 200 into two areas, which are shown at the top and the bottom of FIG. 4. The casing is open toward the right side of FIG. 4. A cover element 240 is inserted into this open end of the casing 210, and together with the cartridge casing 210 borders a fluid channel 241 that connects the two areas of the cartridge.

The area of the cartridge located below in FIG. 4 accommodates a product container 250 in the form of a cartridge with a cylindrical lateral wall area 251 and a product plug 252 that can be displaced therein. At its proximal end, the product container 250 is held in a gasket 242, while at its distal end, the product container 250 is fixed in place by a holding insert 260, an inner ring flange 261 of which presses it against the lateral wall of the product container, which tapers in this area. The distal end of the product container is sealed by a seal 255 with a septum 254.

The area of the cartridge casing 210 situated above in FIG. 4 borders a cylindrical cavity, in which a hydraulic plug 230 is displaceable. The circumference of the head of the hydraulic plug 230 is sealed against the wall of the cartridge casing 210 by an elastic gasket 232, which may be molded onto the head as a single piece in a two-component injection molding process. In this way, the cartridge casing 210, the hydraulic plug 230 and the cover element 240 together border a hydraulic reservoir 231, which incorporates a hydraulic fluid, e.g., dyed, deionized water or a suitable oil. The hydraulic fluid also fills the fluid channel 241 completely, along with the displacement reservoir 243 adjacent thereto. The displacement reservoir is thereby bordered by the lateral wall of the product container 250, the product plug 252 and the cover element 240.

An oblong, cylindrical, hollow-spindle type sleeve 233 with an external outer thread abuts the head of the hydraulic plug 230 in a proximal direction. Situated inside the sleeve 233 is a plurality of longitudinal ribs 234, which run parallel to the longitudinal direction of the sleeve. These can be discerned in FIG. 5. The outer thread of the sleeve 233 engages the internal thread of a spindle nut 270. The spindle nut 270 is held inside the cartridge casing 210 so as to be resistant to torsion, but axially displaceable. A pre-stressed coil spring 280 presses the spindle nut 270 axially in the distal direction, i.e., toward the hydraulic reservoir, against a stop 213. Normally, the spindle nut 270 is fixed relative to the cartridge casing 210 as a result. However, as soon as an axial counterforce acts on the spindle nut 270 in a proximal direction that exceeds a threshold that can be set by the pre-stressing force of the coil spring 280, the spindle nut 270 is displaced axially in the proximal direction. As long as the spindle nut 270 is stationary, the sleeve 233 is guided through the spindle nut 270 opposite the casing 210. Therefore, the spindle nut 270 may also referred to more generally as a guide element.

Figure 6:
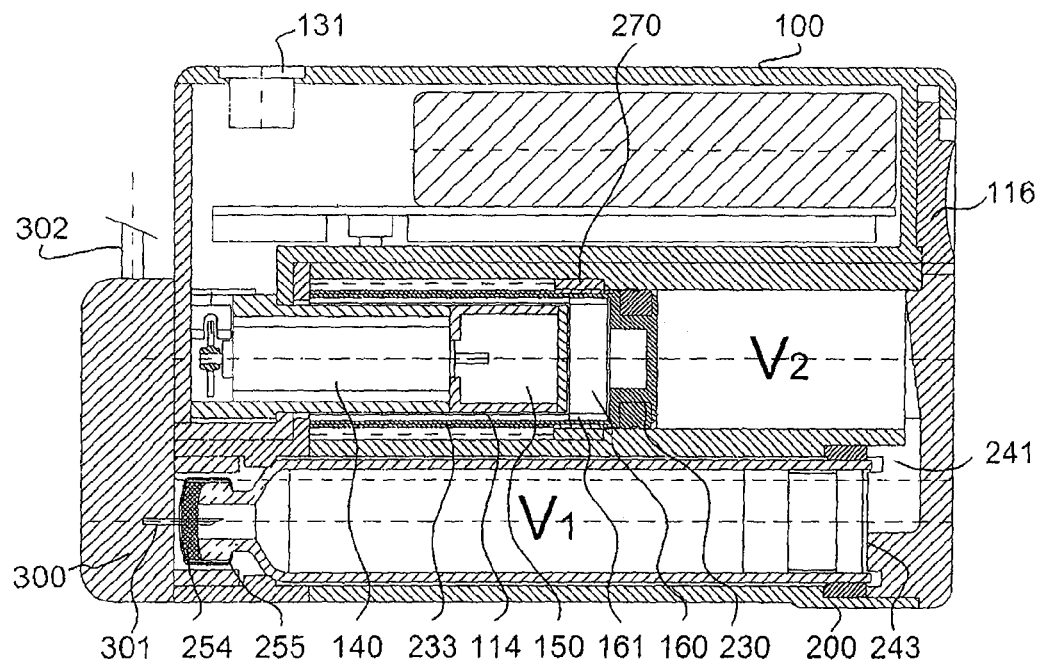
FIG. 6 is a longitudinal sectional view of one embodiment of an administration appliance in accordance with the present invention, comprising a filled cartridge with a base unit.

To administer or dispense the medication in the product container 250, the cartridge 200 is first connected with the base unit 100. The area of the cartridge situated above in FIG. 4 here assumes position in the receiving area 115 of the base unit. FIG. 6 shows the administration appliance assembled in this way. The finger-like area 114 that accommodates the motor 140 and the transmission 150 now extends inside the sleeve 233. In the process, the drive element fingers 161 of the drive element 160 reach into the gap between two respective longitudinal ribs 234, thereby establishing a torsion-resistant, but longitudinally displaceable connection between the drive element 160 and the sleeve 233. The cartridge 200 is fixed on the base unit 100 in axial direction by a displaceable latch 116. The latch 116 is laterally beveled, so that it slides back on its own while inserting the cartridge. The latch is spring-loaded in the latching position, so that it is pressed into the latching position automatically after assembly, and prevents the cartridge from unintentionally detaching from the base unit.

An adapter 300 abutted by a catheter 302 of an infusion set is then placed on the cartridge. The adapter 300 encompasses a hollow needle 301, which punctures the septum 254 of the seal 255, thereby connecting the product container 250 with the catheter 302.

Figure 7:
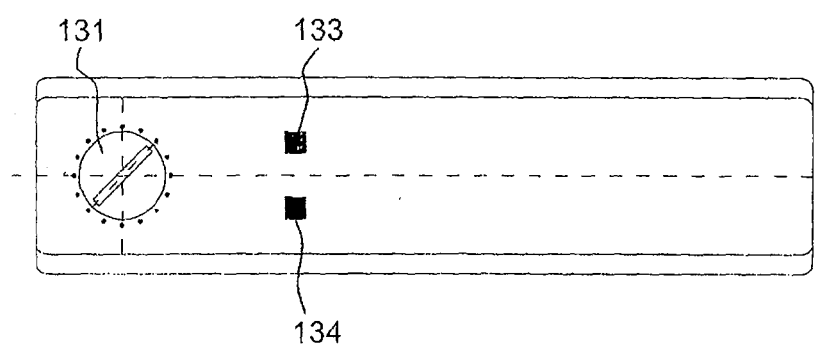
FIG. 7 is a top view of the administration appliance of FIG. 6.
Figure 8:
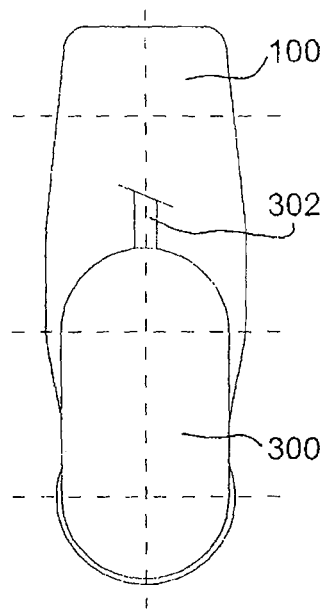
FIG. 8 is a side view of the administration appliance of FIG. 6, as viewed to the right.
Figure 9:
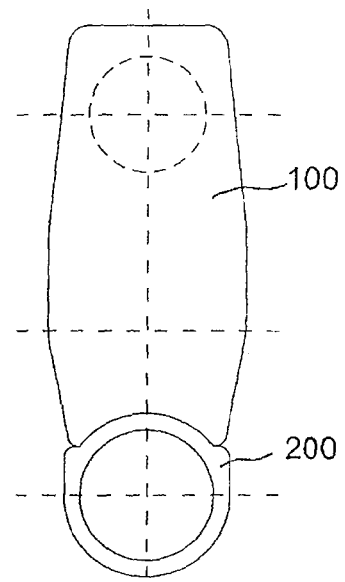
FIG. 9 is the side view of the administration appliance in the view shown in FIG. 8, after removal of the connecting unit.
Figure 10:
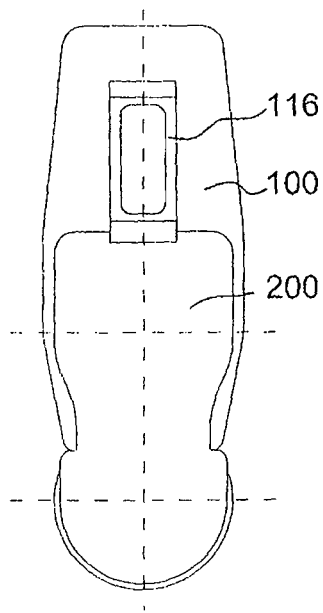
FIG. 10 is a side view of the administration appliance of FIG. 8, as viewed to the left.

The basal rate of medication to be administered is set on a multi-stage rotary switch 131, which is discernible in FIG. 7. The appliance is now activated, and initially performs a self-test. A "priming" switch (not shown in the drawing) is then actuated to dispense a specific quantity of product for the first time, so as to fill the infusion set completely with the medication to be administered, and purge any air that might be present therein ("priming"). An unintentional actuation of this switch is prevented by making this switch difficult to access, and allowing its actuation only by a needle or ballpoint pen tip, for example. As an alternative, priming can also take place automatically when the adapter is set. The appliance then switches to normal operation, during which a specific product quantity is dispensed continuously or in preset intervals (e.g., once or several times an hour). Two light-emitting diodes 133, 134 indicate the operating state of the appliance during all of these processes.

To dispense and administer a product, the motor 140 uses the transmission 150 to displace the drive element 160 so that it rotates. The drive element 160 engages with the longitudinal ribs 234, transmitting this rotational movement to the sleeve 233 and the head of the hydraulic plug 230 connected thereto as a single piece. Since the sleeve 233, with its external thread, is guided into the spindle nut 270, rotating the sleeve 233 also causes a feed movement in the axial direction. As a whole, the hydraulic plug 230 hence performs a screw movement. This reduces the volume $V_2$ of the hydraulic reservoir, so that hydraulic fluid is pressed through the fluid channel 241 into the displacement reservoir 243, causing the product plug to advance in a distal direction. As a result, the fluid product is ejected through the hollow needle 301 and the catheter 302 from the volume $V_1$, which also is diminishing.

Rotating the sleeve 233 hence advances the hydraulic plug 230, thereby indirectly causing the ejection or movement of the fluid product from the product container. Therefore, the hydraulic plug 230 with the sleeve 233 may also be referred to more generally as a transmission element, which transmits the rotational movement generated by the motor into a feed movement. This transmission element is guided in the spindle nut 270 as a guiding element. Only torques around the feed direction are transmitted between the base unit 100 and the cartridge 200, no axial forces. This enables a simple design for the connection between the base unit 100 and the cartridge 200, and the provision of a relatively simple latch 116 that does not have to absorb any significant axial forces. The complementary shape of these units ensures the reliable absorption of torques between the base unit 100 and the cartridge 200 in a simple manner.

Figure 12:
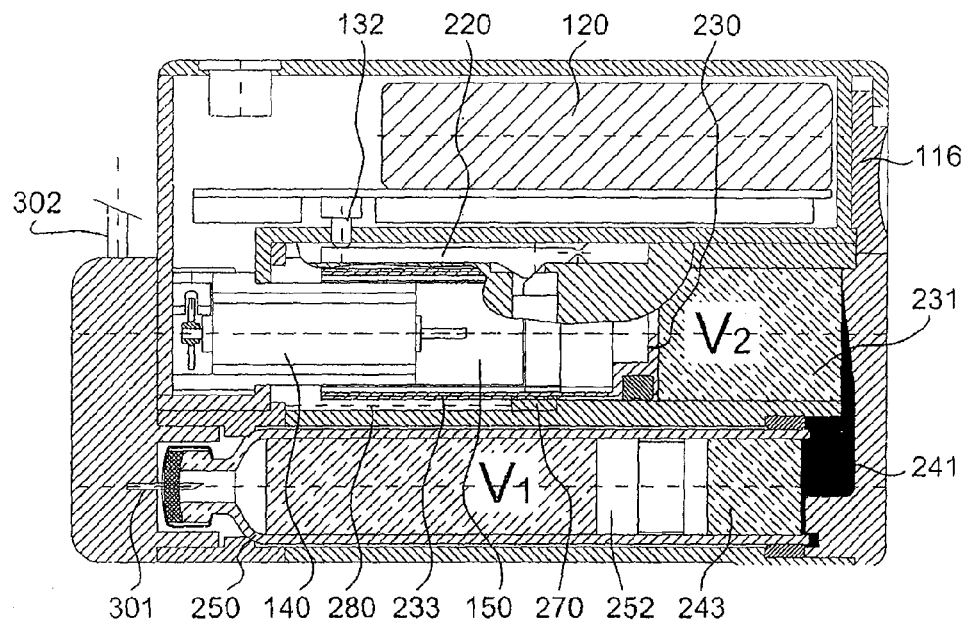
FIG. 12 is a longitudinal sectional view through the administration appliance of FIG. 6, after a portion of the medication contained therein was dispensed, in part diagrammatic and sectionally magnified in the plane B-B of FIG. 11.

FIG. 12 shows the administration appliance after a certain period of operation. The hydraulic plug 230 has now traversed about a fourth of its path or travel. The sleeve 233 continues to envelop the transmission 150 and a part of the motor 140. The advancing hydraulic plug 230 displaced about one fourth of the hydraulic fluid from the hydraulic reservoir 231 into the displacement reservoir 243. As a result, the product plug 252 was also advanced for about one fourth of its path, and a corresponding quantity of medication was ejected from the product container 250.

In some embodiments, after the hydraulic plug 230 is completely advanced, the product container is essentially evacuated or empty. The cartridge may then be replaced. To this end, the adapter 300 is removed, the latch 116 is released, and the cartridge 200 is simply pulled axially out of the base unit 100. The base unit 100 is then immediately ready for the insertion of a new cartridge without having to put back the motor or take any other special measures. As a result, the cartridge can be replaced very easily and quickly. In some preferred embodiments, the base unit 100 has a suitable counter, which registers the number of cartridge replacements, and prevents further operation after a preset number of replacements. This makes it possible to ensure that only a preset number of cartridge replacements can be performed before the battery 120 must be replaced, or the entire base unit 100 must be changed out.

Figure 11:
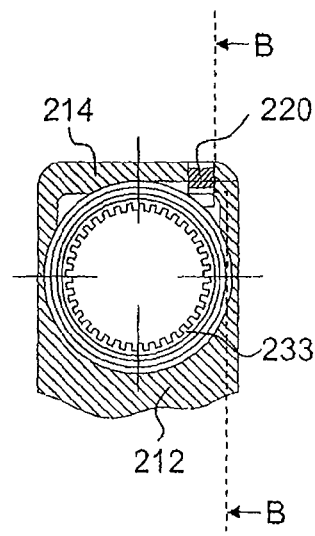
FIG. 11 is a cross sectional view through the cartridge of FIG. 4 in the plane A-A (shown in FIG. 4)
Figure 13:
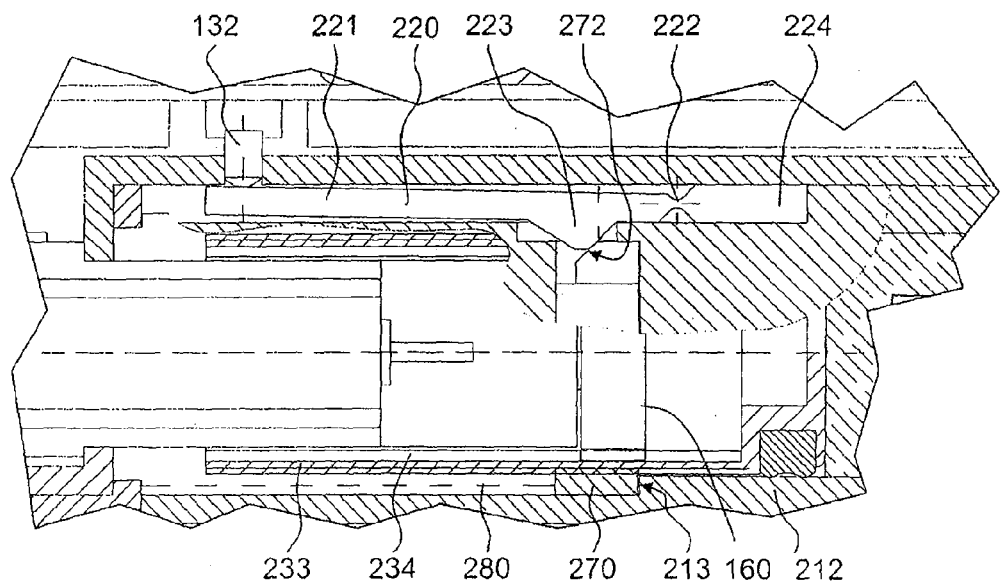
FIG. 13 is a magnified section of FIG. 12.

FIGS. 11 and 13 will now be referenced to explain what happens if the hydraulic plug 230 is prevented from advancing while administering the medication. This feed impediment can have various causes. The reason most often encountered in practice lies in a possible occlusion of the catheter 302, e.g., as the result of foreign bodies or a snapping of the catheter. However, other reasons are conceivable as well. For example, the cartridge may have been completely evacuated, thereby preventing the hydraulic plug from advancing any further. A user might have failed to correctly place the adapter 300, so that the septum of the product container was not punctured, as a result of which no product can exit. Also conceivable is a jamming of the product plug or of the hydraulic plug, or an occlusion in the hydraulic channel 241. In all these examples, it is important that the malfunction or trouble situation be recognized, and that the user be warned accordingly.

In the event of a disruption, the counter-force exerted on the hydraulic plug 230 increases sharply if the motor continues to impart rotation to the sleeve 233, since the disruption impedes the hydraulic plug 230 from advancing further. If the motor continues to rotate the sleeve 233, it causes the spindle nut 270 to instead be pushed back in a proximal direction relative to the casing 210 against the force exerted by the spring 280.

This backward displacement of the spindle nut 270 is detected. To this end, a lever 220 is provided to transmit the proximal (axial) displacement of the spindle nut 270 to a lateral (radial) movement of the lever, and actuate a switch 132 in the base unit. Actuating the switch 132 turns off the drive and triggers an alarm, which alerts the user that a malfunction has occurred.

This lever can be discerned in FIGS. 11 to 13. The lever is shown in a highly schematic cross section in FIGS. 12 and 13, which runs through the plane B-B of FIG. 11.

A relatively long, stretched out recess that runs or extends in the longitudinal direction is provided laterally offset relative to the longitudinal axis in the casing wall 214 of the cartridge 200 facing the holding area 111 of the base unit 100. This recess accommodates the lever 220, which is designed as a single piece with the cartridge casing. The pivoting axis of this lever is formed by a taper 222 near the distal end of the recess. Both lever arms of the lever are arranged on the same side of this pivoting axis. The first "long" lever arm proceeds from the taper 222 and extends parallel to the casing wall inside the recess until close to its proximal end. The second "short" lever arm proceeds from the taper 222 and first coincides with the first lever arm, but ends in a catch 223 that extends form the first lever arm laterally into the cartridge 200. Since this arm is considerably shorter than the first lever arm 221, just a slight lateral displacement of the catch toward the exterior of the casing results in a relatively large lateral displacement of the free end of the first lever arm. The catch 223 acts in conjunction with the spindle nut 270 in such a way that a proximal (axial) displacement of, the spindle nut 270 leads to a lateral (radial) pivoting of the lever 220. To this end, both the exterior of the spindle nut 270 and the catch 223 are beveled in such a way that a proximal displacement of the spindle nut 270 causes a lateral evasive movement of the catch 233.

The switch 132 is secured in the base unit 100 adjacent to the free end of the long lever arm 221. In this way, the pivoting of the lever 220 in a lateral direction leads to an actuation of the switch 132. The switch 132 can be a simple mechanical switch or a suitable type of proximity sensor, e.g., one which operates for example in a capacitive or inductive manner, as a pressure sensor or optically. In some preferred embodiments, the switch may be liquid-tight in design, thereby preventing water or other liquids from penetrating into the base unit.

The cartridge can be manufactured in a cost-effective manner by arranging the switch in the base unit 100 and providing a purely mechanical arrangement in the cartridge 200. In addition, no electrical connections are required between the cartridge and the base unit.

In some embodiments, the administration appliance exhibits an innovative sealing concept. The interior of the base unit 100 along with the liquid-carrying areas of the cartridge 200 are each liquid-tight, and in some embodiments, also gas-tight, relative to the environment. By contrast, no sealing measures are taken between the base unit 100 and cartridge 200 by design. This further simplifies cartridge replacement, since the patient does not have to make sure that a correct sealing takes place when inserting a new cartridge. In addition, a reliable seal is achieved for the separate individual units or modules (base unit and cartridge), since sealing takes place at the factory, where it typically can be accomplished with more reliability than possible for patients in day-to-day use. Another advantage becomes evident when considering how the hydraulic plug with sleeve moves in the cartridge casing. The screw movement of these parts causes the volume included between the cartridge and base unit to increase during operation, since the hydraulic plug is moving into the cartridge. If the cartridge and the base unit were sealed relative to each other, a vacuum would arise to counter any further advance by the hydraulic plug. Not providing a seal between the cartridge and the base unit allows ambient air to get into this gap. By contrast, the increasing volume is often situated in an area sensitive to penetrating liquids in administration appliances in prior art. For this reason, special sealing measures are often implemented there using liquid-tight, but gas-permeable membranes. The present sealing concept eliminates this related outlay. In addition, the present sealing concept offers greater flexibility when designing the base unit and the cartridge, since no attention need be focused on a mutual seal. Further, the structural design of the proposed administration appliance makes the latter impervious to air pressure fluctuations.

Several structural characteristics and variants of the administration appliance will additionally be covered below.

Figure 14:
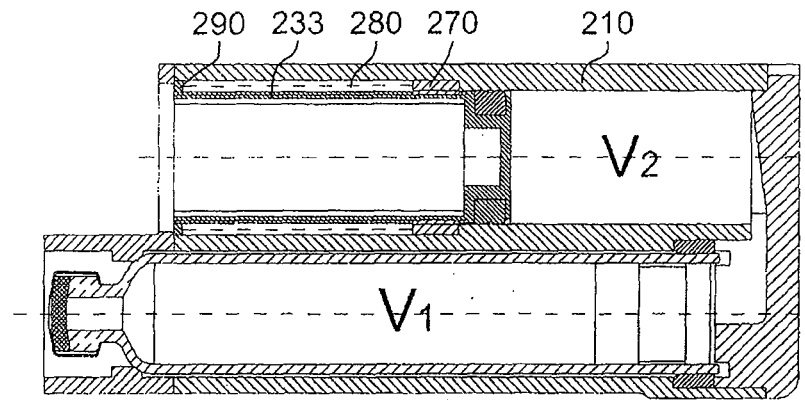
FIG. 14 is a longitudinal sectional view through a cartridge in an alternative embodiment.
Figure 15:
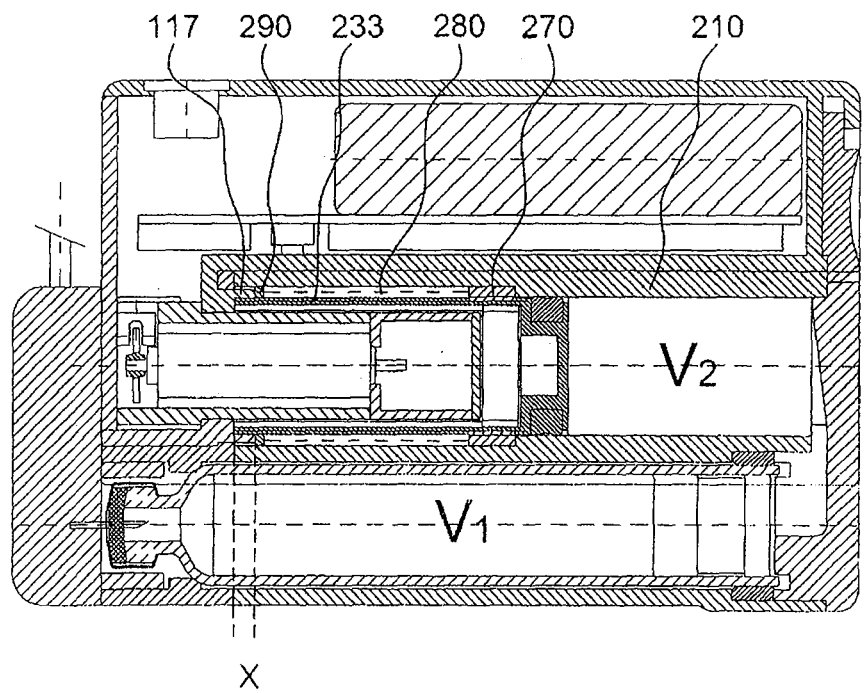
FIG. 15 is a longitudinal sectional view through an administration appliance with the cartridge of FIG. 14.

FIGS. 14 and 15 show a variant of the administration appliance in accordance with the present invention in which the pre-stress of the spring 280 is relatively low for as long as the cartridge is not yet connected with the base unit, and is only increased as the cartridge is connected with the base unit. To this end, the cartridge exhibits a support ring 290 that can shift in the distal direction as a support for the proximal end of the spring 280. Therefore, the spring is arranged between the ring and the spindle nut 270. As long as the cartridge is not connected with the administration appliance, the spring presses the support ring in the proximal direction against a casing stop, as evident from FIG. 14. As discernible from FIG. 15, the base unit 100 in this variant exhibits an annular projection 117 of the casing that extends in the distal direction, and is dimensioned in such a way that it slides into the space between the outer wall of the cartridge casing 210 and the sleeve 233 during insertion of the cartridge 200. When the cartridge is connected with the base unit, the support ring 290 is as a result shifted in the distal direction, thereby compressing the spring 280. The displacement path is marked X in FIG. 15. In the present example, it is relatively small, but a larger one can be selected without any problem.

An advantage to this arrangement is that a volume increase due to a temperature rise, which can arise during storage of the cartridge, can be compensated. Since, upon a rise in pressure, the spindle nut 270 can deflect in the proximal direction against the still relatively small spring power, it permits an increase in volume in the product container and hydraulic reservoir with only a slight counter-pressure. For example, a temperature rise of 20° C. leads to a volume increase of approx. 6 parts per mill in aqueous solutions. If it were not possible to balance out this volume increase, a corresponding significant internal pressure would result in the hydraulic reservoir and in the product container. The present arrangement is effective at avoiding such a pressure rise.

The embodiment described above exhibits a lever mechanism and a switch that works in conjunction with it, so as to transmit and detect a proximal displacement of the spindle nut 270. However, other possibilities are also conceivable for detecting the displacement of the spindle nut. For example, electricity can be used to directly detect a displacement by arranging an electrical contact proximal to the spindle nut at a small distance, which contact is closed when the spindle nut shifts. For this purpose, an electrical connection may be established between the cartridge and the base unit, e.g., by a contact pair. Also conceivable is a proximity sensor, e.g., a capacitive, inductive or optical sensor, which is accommodated directly in the cartridge.

In the embodiment described above, the head of the hydraulic plug 230 and the sleeve 233 form a rigid unit. The entire stopper is fabricated as a single piece, in, for example, a two-component injection molding procedure. The sleeve in conjunction with the thread and the longitudinal ribs may be made out of a hard, torsion-resistant plastic, while the head of the hydraulic plug 230 consists entirely or partially of a soft, elastically deformable plastic, e.g. a thermoplastic elastomer. In the exemplary embodiment described above, for example, only the gasket 232 consists of such a soft material.

However, in some embodiments, the hydraulic plug and the sleeve can instead be fabricated in two pieces. The sleeve can be rotatable relative to the plug. In this way, the screw movement of the sleeve can be converted into a purely translational feed movement of the plug.

In the example described above, the motor 140 is coaxially arranged with the transmission 150. However, various other configurations are possible. For example, the motor with its shaft can be situated parallel to the feed direction in the holding area 111 of the base unit. Gearwheels can then be used for transmitting the drive movement. Also conceivable is an arrangement at an angle of 90 degrees to the feed direction, wherein the rotational movement could then be transmitted by bevel gearwheels. Use could also be made of motors with a shaft guided out of the motor casing on only one side. The encoder can then be arranged between the motor and the transmission.

Various types of commercially available electric motors can be used as the motor, e.g., a DC motor, a stepping motor or a piezoelectric drive.

In the embodiments described above, the battery used to supply power to the control electronics and to the drive motor is accommodated in the reusable base unit. For this reason, the same battery is generally used for administering the content of a larger number of cartridges. The battery might not be replaceable, and may be used as a power supply for the entire life of the appliance. However, this may require a relatively large and heavy battery. Therefore, a variant can also provide that the battery be accommodated in the cartridge. Two or more electrical contacts are provided in this case to establish an electrical connection between base unit and cartridge. This achieves a certain savings in weight and space. Since the battery is already incorporated in the cartridge at the factory, this also ensures that a fresh battery is always present.

The achievable weight and space savings can be illustrated by way of an example: A modern Li battery sufficient for administering approximately 50 carpules with 3 ml of medication each typically weighs approx. 20 g. By contrast, a simple silver oxide battery of the kind that could be placed in the cartridge weighs only approx. 4 g. This corresponds to only about one fifth of the weight of the Li battery.

In order to simplify battery assembly and enable an environmentally safe disposal, the battery can be accommodated in a drawer that is easy to remove from outside. In this case, the drawer with the battery could be incorporated just before delivery to the patient, or even by the patient him/herself, if so desired.

In the embodiment described above, a hydraulic transmission of power takes place between the transmission element, which is driven by the drive element of the base unit, and the product container. The hydraulic path is here used not to control the administration rate, but only to achieve a space-saving, cost-effective and reliable deflection of drive power. Different variants of such a hydraulic power transmission are described in Application PCT/CH 2006/000258 dated May 15, 2006, the disclosure of which is incorporated herein by reference. The noted application discloses other advantages and structural details of hydraulic power transmission, along with different variants for configuring the product container and the hydraulic reservoir, which can also be used in conjunction with the present invention.

The product container can be designed as a container that is entirely compressible instead of as a carpule. For example, the container can exhibit a bellows-like lateral wall, an expansible portion, or be bag-like. The same holds true for the hydraulic reservoir. It is also conceivable for the rotational movement to be transmitted to the hydraulic reservoir simply by quasi "wringing out" a flexible hydraulic container by twisting its proximal end relative to the distal end.

Another variant omits hydraulic power transmission. For example, the product plug can replace the hydraulic plug in the exemplary embodiment described above, i.e., the product plug is then shifted directly by the sleeve 233. While this necessitates some structural changes, it also simplifies the structure. Also conceivable is to deflect the advancing sleeve 233 to advance the product plug, e.g., via a flexible, bendable piston rod.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An appliance for administering a fluid product, comprising:

a reusable base unit comprising a drive device, and a replaceable cartridge detachably connectable with the base unit and comprising a product container for the fluid product, wherein the base unit further comprises a drive element able to be moved by the drive device in a rotational movement around a rotational axis, wherein the cartridge further comprises a movable transmission element complementary to the drive element and having an external thread for guiding movement of the transmission element, wherein the rotational movement of the drive element causes the transmission element to move, guided by the external thread, in a screwing movement comprising an axial movement and a rotational movement, said screwing movement causing an ejection of the fluid product from the product container, wherein the drive element and the transmission element are able to be detachably connected to each other for transmitting the rotational movement, and wherein the transmission element comprises a sleeve with an inside, the sleeve at least partially enveloping the drive element when the cartridge is connected with the base unit, and engaging the drive element on the inside.

2. The appliance according to claim 1, wherein the inside of the sleeve has one or more longitudinal grooves or longitudinal ribs extending generally parallel to the rotational axis, and wherein the outside of the drive element has a structure suitable for engaging the longitudinal grooves or longitudinal ribs.

3. The appliance according to claim 2, wherein the transmission element is able to be moved between an initial position assumed by the transmission element before evacuation of the product container begins and a final position assumed by the transmission element after the product container has been emptied, and wherein the transmission element envelops at least part of the drive device, at least in the initial position.

4. The appliance according to claim 3, wherein the drive device comprises an electric motor and a transmission connected thereto to transmit a drive movement of the motor into a rotational movement of the drive element, wherein the motor and the transmission are arranged coaxially along the rotational axis, and wherein the transmission element envelops at least a part of the transmission, at least in the initial position.

5. The appliance according to claim 1, wherein the drive device is accommodated at least in part in a finger-like area of the base unit extending along the rotational axis, and wherein the cartridge, when assembled, at least partially envelops the finger-like area.

6. The appliance according to claim 5, wherein the base unit comprises a holding area that is laterally spaced relative to the finger-like area, and wherein the cartridge, when secured to the base unit, comprises an area arranged between the finger-like area and the holding area in a lateral direction to achieve a torsion-resistant connection between the cartridge and the base unit.

7. The appliance according to claim 1, wherein the cartridge comprises a fluid reservoir with a movable plug, and wherein the transmission element is connected with the plug such that rotating the transmission element advances the plug.

8. The appliance according to claim 7, wherein the plug is fabricated as a single piece with the transmission element.

9. An appliance for administering a fluid product, comprising:

a reusable base unit comprising a drive device, and a replaceable cartridge detachably connectable with the base unit and comprising a product container for the fluid product, wherein the base unit further comprises a drive element able to be moved by the drive device in a rotational movement around a rotational axis, wherein the cartridge further comprises a movable transmission element complementary to the drive element and having an external thread for guiding movement of the transmission element, wherein the rotational movement of the drive element causes the transmission element to move, guided by the external thread, in a screwing movement comprising an axial movement and a rotational movement, said screwing movement causing an ejection of the fluid product from the product container, wherein the drive element and the transmission element are able to be detachably connected to each other for transmitting the rotational movement, the cartridge comprising a fluid reservoir with a movable plug and the transmission element connected with the plug such that rotating the transmission element advances the plug, and wherein the fluid reservoir is a hydraulic reservoir containing a hydraulic fluid, and the cartridge additionally comprises a hydraulic connection between the hydraulic reservoir and a displacement reservoir that acts in conjunction with the product container, wherein the hydraulic reservoir, the hydraulic connection and the displacement reservoir are arranged such that the advancing movement of the plug moves the hydraulic fluid from the hydraulic reservoir through the hydraulic connection and into the displacement reservoir, thereby causing the ejection of the fluid product from the product container.

10. The appliance according to claim 1, wherein the transmission element comprises a sleeve with an external surface and a length, and the external thread extending substantially the entire length of the sleeve.

11. The appliance according to claim 10, wherein the sleeve is cylindrical.

12. The appliance according to claim 1, further comprising a guide element carried by the cartridge, the guide element adapted to receive the transmission element and having an internal thread complementing the external thread of the transmission element.

13. The appliance according to claim 12, wherein an axial displacement of the guide element causes an alarm signal.

14. The appliance according to claim 12, further comprising a signaling arrangement for signaling an abnormal operating condition of the appliance, the signaling arrangement comprising the guide element being in a selected axial position relative to the cartridge, a sensor and a signal generator operably coupled to the sensor, wherein if the sensor detects an axial movement of the guide element away from the selected axial position, the signal generator generates a signal.

15. An appliance for administering a fluid product, comprising:

a reusable base unit comprising a drive device, and a replaceable cartridge detachably connectable with the base unit and comprising a product container for the fluid product, wherein the base unit further comprises a drive element non-detachably coupled to the base unit and able to be moved by the drive device in a rotational movement around a rotational axis, wherein the cartridge further comprises a movable transmission element non-detachably coupled to the cartridge and complementary to the drive element and having an external thread for guiding movement of the transmission element, wherein the rotational movement of the drive element causes the transmission element to move, guided by the external thread, in a screwing movement comprising an axial movement and a rotational movement, said screwing movement causing an ejection of the fluid product from the product container, and wherein the drive element and the transmission element are able to be detachably connected to each other for transmitting the rotational movement, said appliance further comprising:

a guide element carried by the cartridge, the guide element adapted to receive the transmission element and having an internal thread complementing the external thread of the transmission element, and a signaling arrangement for signaling an abnormal operating condition of the appliance, the signaling arrangement comprising the guide element being in a selected axial position relative to the cartridge, a sensor and a signal generator operably coupled to the sensor, wherein if the sensor detects an axial movement of the guide element away from the selected axial position, the signal generator generates a signal, wherein the guide element is a spindle nut.

16. The appliance according to claim 1, wherein a succession of said cartridges are connectable to and detachable from said base unit.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,679,070 B2 | |
| APPLICATION NO. | : 12/541243 | |
| DATED | : March 25, 2014 | |
| INVENTOR(S) | : Clavadetscher et al. | |

It is certified that error appears in the above-identified patent and that said Letters Patent is hereby corrected as shown below:

IN THE SPECIFICATION

| Column | Line | | Should Read |
|---|---|---|---|
| 2 | 24 | a base unit and a relaceable cartridge | a base unit and a replaceable cartridge |
| 9 | 62 | (axial) displacement of, the spindle | (axial) displacement of the spindle |

Signed and Sealed this
First Day of July, 2014

Michelle K. Lee
*Deputy Director of the United States Patent and Trademark Office*